(12) United States Patent
Mirza et al.

(10) Patent No.: US 10,575,867 B2
(45) Date of Patent: Mar. 3, 2020

(54) SHIELD FOR ENDOSCOPIC SURGICAL BLADE AND METHOD OF USE

(71) Applicant: A.M. SURGICAL, INC., Smithtown, NY (US)

(72) Inventors: Romi Mirza, Smithtown, NY (US); Ather Mirza, Smithtown, NY (US)

(73) Assignee: A.M. SURGICAL, INC., Smithtown, NY (US)

( * ) Notice: Subject to any disclaimer, the term of this patent is extended or adjusted under 35 U.S.C. 154(b) by 532 days.

(21) Appl. No.: 14/947,705

(22) Filed: Nov. 20, 2015

(65) Prior Publication Data

US 2017/0143364 A1     May 25, 2017

(51) Int. Cl.
*A61B 17/32* (2006.01)
*A61B 17/3211* (2006.01)
*A61B 17/00* (2006.01)

(52) U.S. Cl.
CPC ............... *A61B 17/320036* (2013.01); *A61B 2017/00907* (2013.01); *A61B 2017/32113* (2013.01)

(58) Field of Classification Search
CPC .. A61B 17/320036; A61B 2017/00907; A61B 2017/32113
See application file for complete search history.

(56) References Cited

U.S. PATENT DOCUMENTS

| | | | | |
|---|---|---|---|---|
| 40,163 A | * | 10/1863 | Fitch | B26B 27/00 30/294 |
| 686,712 A | * | 11/1901 | Carley | B26B 3/00 30/165 |
| 4,026,295 A | * | 5/1977 | Lieberman | A61B 17/32 606/167 |
| 4,432,138 A | * | 2/1984 | Piccolo, Jr. | B26B 27/00 30/294 |
| 5,139,507 A | * | 8/1992 | Dolgin | A61B 17/3211 30/151 |
| 5,273,024 A | * | 12/1993 | Menon | A61B 17/3417 128/898 |
| 5,282,816 A | * | 2/1994 | Miller | A61B 17/1659 606/167 |
| 5,346,503 A | * | 9/1994 | Chow | A61B 1/317 30/314 |
| 5,387,222 A | * | 2/1995 | Strickland | A61B 17/320036 30/294 |
| 5,413,580 A | * | 5/1995 | Stephenson | A61B 17/320036 30/315 |

(Continued)

OTHER PUBLICATIONS

International Search Report, International Preliminary Report on Patentability and Written Opinion, issued in International Patent Application No. PCT/US2015/061950, dated Apr. 7, 2016.

*Primary Examiner* — Julie A Szpira
(74) *Attorney, Agent, or Firm* — Ping Wang; Morris, Manning & Martin, LLP

(57) ABSTRACT

A shield component for an endoscopic surgical blade is disclosed. An endoscopic surgical blade assembly is disclosed. The endoscopic surgical blade assembly contains an endoscopic surgical blade having a distal end, a proximal end, a top edge, a bottom edge and one or more cutting surfaces at the distal end, and a protective shield attached to the blade above the one or more cutting surfaces and extending away from the distal end of the blade. The blade is structurally configured for attachment to the distal end of an endoscope.

14 Claims, 3 Drawing Sheets

(56) References Cited

U.S. PATENT DOCUMENTS

| | | | | |
|---|---|---|---|---|
| 5,549,623 A * | 8/1996 | Sharpe | A61B 17/320016 | 600/564 |
| 5,569,299 A | 10/1996 | Dill et al. | | |
| 5,620,446 A * | 4/1997 | McNamara | A61B 17/320036 | 128/898 |
| 5,667,519 A * | 9/1997 | Ramsey | A61B 17/320016 | 606/167 |
| 5,681,262 A * | 10/1997 | Isse | A61B 1/012 | 600/104 |
| 5,792,162 A * | 8/1998 | Jolly | A61B 17/32 | 30/151 |
| 5,800,449 A | 9/1998 | Wales | | |
| 5,827,311 A * | 10/1998 | Berelsman | A61B 17/320036 | 606/167 |
| 5,908,433 A * | 6/1999 | Eager | A61B 90/30 | 606/170 |
| 5,928,138 A * | 7/1999 | Knight | A61B 17/00008 | 600/104 |
| 6,070,326 A * | 6/2000 | Berns | B26B 29/02 | 30/2 |
| 6,626,925 B2 * | 9/2003 | Newman | A61B 17/3213 | 30/151 |
| 6,685,717 B1 * | 2/2004 | Ilic | A61B 17/320036 | 606/167 |
| 7,153,317 B2 * | 12/2006 | Kanodia | A61B 17/3211 | 606/167 |
| D631,161 S * | 1/2011 | DaSilva | D24/147 | |
| 8,221,422 B2 * | 7/2012 | Mangione | A61B 17/320016 | 606/167 |
| 8,523,892 B2 * | 9/2013 | Rehnke | A61B 1/313 | 600/104 |
| 8,608,763 B1 * | 12/2013 | Jurbala | A61B 17/320036 | 606/170 |
| 8,771,303 B1 * | 7/2014 | Jurbala | A61B 17/320036 | 606/170 |
| 8,858,544 B2 * | 10/2014 | McNally | A61B 17/3209 | 606/27 |
| 8,992,424 B2 * | 3/2015 | Orbay | A61B 1/00048 | 600/183 |
| 9,144,433 B2 * | 9/2015 | Mirza | A61B 17/320036 | |
| 2005/0033338 A1 * | 2/2005 | Ferree | A61B 17/3201 | 606/167 |
| 2006/0190021 A1 * | 8/2006 | Hausman | A61B 17/320016 | 606/167 |
| 2006/0241665 A1 * | 10/2006 | Bosley | A61B 17/320016 | 606/167 |
| 2007/0045379 A1 | 3/2007 | Shelton, IV | | |
| 2007/0225740 A1 * | 9/2007 | Suddaby | A61B 17/3211 | 606/170 |
| 2007/0288043 A1 * | 12/2007 | Rehnke | A61B 1/313 | 606/170 |
| 2008/0195128 A1 * | 8/2008 | Orbay | A61B 1/00048 | 606/170 |
| 2008/0249556 A1 * | 10/2008 | Yamatani | A61B 17/00008 | 606/190 |
| 2008/0255600 A1 * | 10/2008 | Braam | A61B 17/00008 | 606/190 |
| 2010/0152757 A1 | 6/2010 | Slater | | |
| 2011/0046652 A1 * | 2/2011 | Rehnke | A61B 1/313 | 606/170 |
| 2011/0130779 A1 * | 6/2011 | Mirza | A61B 1/018 | 606/170 |
| 2014/0081081 A1 | 3/2014 | Mirza et al. | | |
| 2016/0128714 A1 * | 5/2016 | DaSilva | A61B 17/320036 | 606/170 |

* cited by examiner

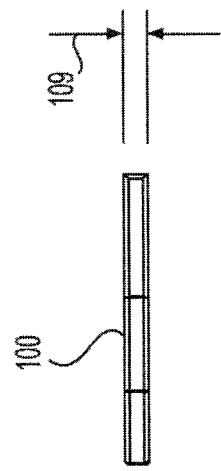
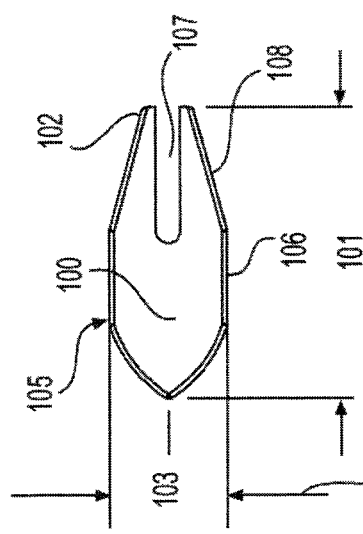
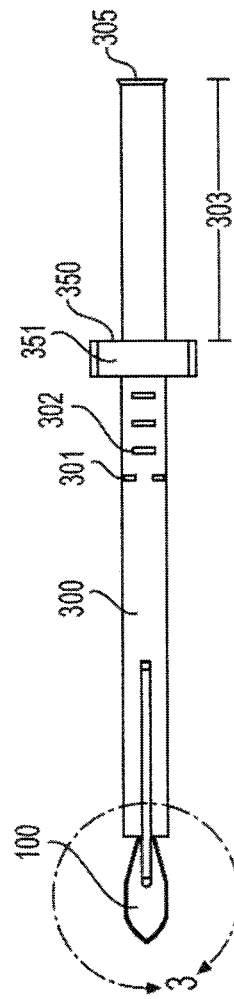
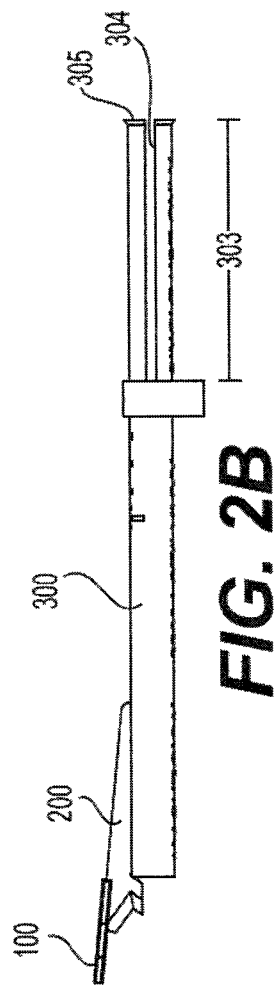

SHIELD FOR ENDOSCOPIC SURGICAL BLADE AND METHOD OF USE

FIELD

This application generally relates to medical devices. In particular, the application relates to devices and methods for endoscopic surgery.

BACKGROUND

Endoscopic surgery is a minimally invasive surgical procedure that is performed through small incisions or natural body openings. An endoscopic procedure typically involves use of specialized devices and remote-control manipulation of instruments with indirect observation of the surgical field through an endoscope or similar device. Comparing to open surgery, endoscopic surgery may result in shorter hospital stays, or allow outpatient treatment.

Endoscopic division of a ligament, tunnel or pulley requires the precise insertion of a cutting implement. In order to implement the procedure, a cannula is inserted into an entry portal, which may be an incision or a natural body opening, and brought into contact with the target tissue. A cutting instrument is then brought into contact with the target tissue and drawn through the tissue in order to divide it.

The body contains many different tissues that are necessarily in close contact with one another. During an endoscopic division of a target tissue, the cannula protects the surrounding tissues on the same side of the target tissue from damage. However, frequently a target tissue is in close proximity to, or contact with, an overlying tissue opposite the cannula that may be damaged by the cutting instrument. Accordingly, there exists a need in the art for an endoscopic cutting instrument with a component that prevents the damage of tissues overlying a target tissue.

The present application provides a shield component that fulfils this need by attaching to the top surface of a cutting instrument and intervening between the target tissue and overlying tissue during an endoscopic division procedure, thereby preventing damage to the overlying tissue.

SUMMARY

One aspect of the present application relates to an assembly comprising an endoscopic surgical blade and a shield component, wherein said shield component attaches to the top edge of a surgical blade in a plane that is perpendicular to the cutting surface of the blade and wherein the longer axis of the shield component extends horizontally in the proximal and distal directions and the shorter axis of the shield component extends horizontally in each lateral direction, and wherein the blade is sized to fit at a tip of an endoscope.

Another aspect of the present application relates to an endoscopic knife assembly, comprising: a knife tube having a distal end and a proximate end, a blade mounted at the distal end of the knife tube and a shield component, wherein said shield component attaches to the top edge of a surgical blade in a plane that is perpendicular to the cutting surface of the blade and wherein the longer axis of the shield component extends horizontally in the proximal and distal directions and the shorter axis of the shield component extends horizontally in each lateral direction, and wherein the blade is sized to fit at a tip of an endoscope.

Another aspect of the present application relates to a shield component for an endoscopic surgical blade, the shield component being flattened and oblong, wherein said shield component attaches to the top edge of a surgical blade in a plane that is perpendicular to the cutting surface of the blade and wherein the longer axis of the shield component extends horizontally in the proximal and distal directions and the shorter axis of the shield component extends horizontally in each lateral direction.

Another aspect of the present application relates to an instrument kit for implementing an endoscopic surgical procedure comprising: an endoscopic knife assembly, comprising: a knife tube having a distal end and a proximate end, a blade mounted at the distal end of the knife tube and a shield component, wherein said shield component attaches to the top edge of a surgical blade in a plane that is perpendicular to the cutting surface of the blade and wherein the longer axis of the shield component extends horizontally in the proximal and distal directions and the shorter axis of the shield component extends horizontally in each lateral direction, and wherein the blade is sized to fit at a tip of an endoscope.

Another aspect of the present application relates to a method for uniportal endoscopic division of a target tissue, comprising: establishing an entry portal at a location proximate to and proximal or distal of the target tissue; inserting a cannula having open proximal and distal ends and an open slot extending along the length of the cannula; inserting an endoscopic viewing device into the cannula, said endoscopic viewing device comprising an endoscopic knife assembly, comprising: a knife tube having a distal end and a proximate end, a blade mounted at the distal end of the knife tube and a shield component, wherein said shield component attaches to the top edge of a surgical blade in a plane that is perpendicular to the cutting surface of the blade and wherein the longer axis of the shield component extends horizontally in the proximal and distal directions and the shorter axis of the shield component extends horizontally in each lateral direction, and wherein the blade is sized to fit at a tip of an endoscope; advancing said endoscopic viewing device so that the blade moves in contact with the target tissue through the slot; operatively engaging the target tissue with the blade such that the shield component contacts the target tissue on the side opposite the cannula thereby intervening between the target tissue and an overlying tissue; and advancing the blade through the cannula to divide the target tissue.

BRIEF DESCRIPTION OF THE DRAWINGS

The present invention can be better understood by reference to the following drawings. The drawings are merely exemplary to illustrate certain features that may be used singularly or in combination with other features and the present invention should not be limited to the embodiments shown.

FIGS. 1A-B illustrate an embodiment of a shield component of an endoscopic knife assembly. FIG. 1A depicts a top view of the shield component. FIG. 1B is a side view of the shield component.

FIGS. 2A-B illustrate an embodiment of an endoscopic knife assembly comprising a shield component. FIG. 2A depicts a top view of an endoscopic knife assembly comprising a shield component. FIG. 2B is a side view of an endoscopic knife assembly comprising a shield component.

FIG. 5A depicts a side view of a low profile cover. FIG. 5B is a bottom view of a low profile cover. FIG. 5C is a proximal end view of a low profile cover.

DETAILED DESCRIPTION

Figure 4:
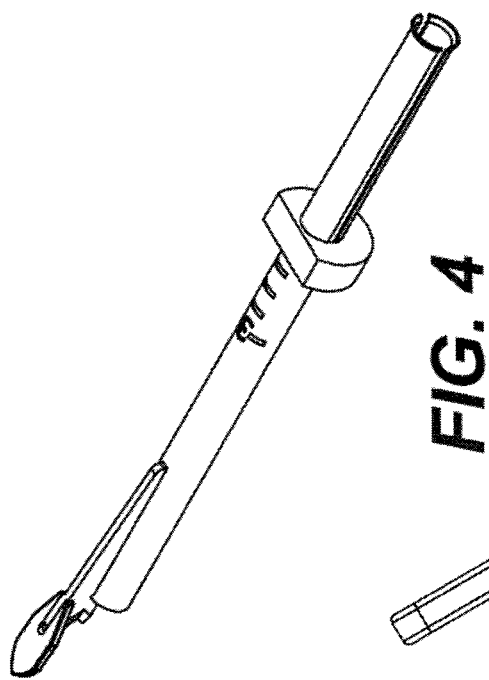
FIG. 4 is an isometric view of an embodiment of an endoscopic knife assembly comprising a shield component.
Figure 5A:
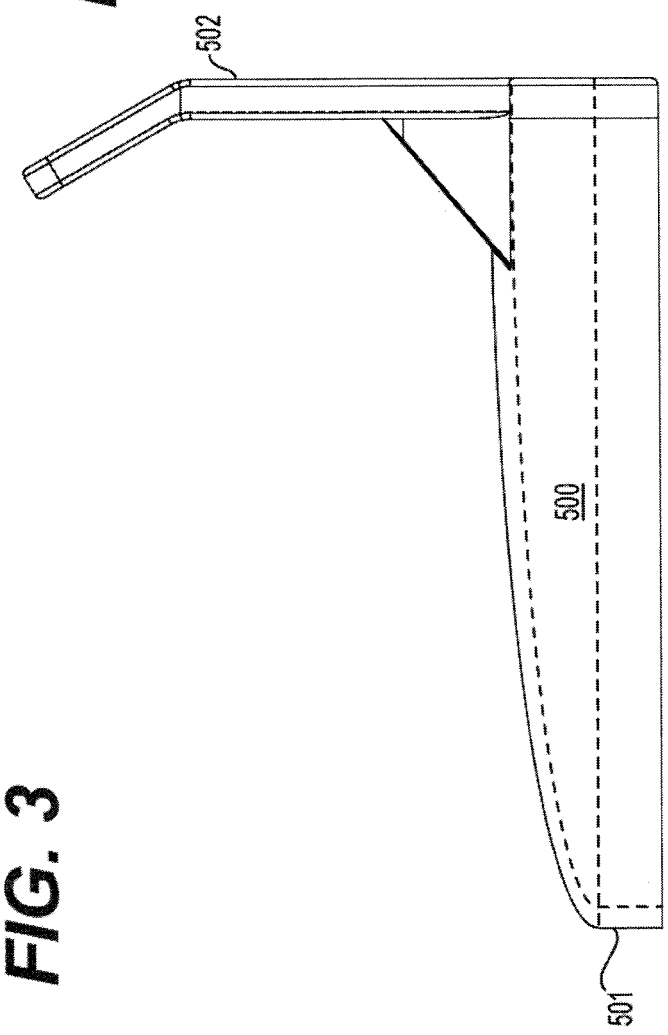
FIGS. 5A-C illustrate an embodiment of a low profile cover for an endoscopic knife assembly comprising a shield component.

The following detailed description is presented to enable any person skilled in the art to make and use the invention. For purposes of explanation, specific nomenclature is set forth to provide a thorough understanding of the present invention. However, it will be apparent to one skilled in the art that these specific details are not required to practice the invention. Descriptions of specific applications are provided only as representative examples. The present invention is not intended to be limited to the embodiments shown, but is to be accorded the widest possible scope consistent with the principles and features disclosed herein.

This description is intended to be read in connection with the accompanying drawings, which are to be considered part of the entire written description of this application. The drawing figures are not necessarily to scale and certain features of the application may be shown exaggerated in scale or in somewhat schematic form in the interest of clarity and conciseness. In the description, relative terms such as "front," "back," "up," "down," "top," "bottom," "upper," "lower," "distal," and "proximate" as well as derivatives thereof, should be construed to refer to the orientation as then described or as shown in the drawing figure under discussion. These relative terms are for convenience of description and normally are not intended to require a particular orientation. Terms concerning attachments, coupling and the like, such as "connected," "mounted," and "attached," refer to a relationship wherein structures are secured or attached to one another either directly or indirectly through intervening structures, as well as both movable or rigid attachments or relationships, unless expressly described otherwise. Features of the present device and method which are described as separate "embodiments" are understood to be combinable where said combination is practicable.

The shield component described herein is a protective shield that is attached to the top edge of a blade for dividing a target tissue in an animal body, such as a ligament, tunnel or pulley. The shield is located above the cutting surface of the blade in order to prevent the cutting of tissues located above the target tissue. The shield extends forward of the cutting surface of the blade, laterally in both directions from the blade and back along the top surface of the blade, thereby providing a protective barrier above the cutting surface of the blade in order to prevent damage to overlying tissue. In some instances, the leading edge of the shield also serves to gently separate overlying tissue from the target tissue.

The shield of the present application can be used with any design of endoscopic surgical blade. In some embodiments, said blade is a blade that will cut when advanced distally from the operator in order to contact and divide the target tissue. In other embodiments, said blade is a blade that will cut when withdrawn proximally toward the operator in order to contact and divide the target tissue.

Endoscopic surgical procedures that can be performed with a cannula or device of the present application include, but are not limited to, any endoscopic division of a target tissue in a body, including where there is an overlying tissue for which protection from damage is desired.

Exemplary procedures include, but are not limited to, carpal tunnel release, Guyon's canal (or tunnel) release, cubital tunnel release, plantar fascia release, lateral release for patella realignment, release of radial tunnel, release of pronatar teres, release of trigger finger (also known as "trigger digit," "trigger thumb," and "stenosing tendovaginitis"), release of lacertus fibrosus, release of the extensor tendons for lateral epicondylitis, release of medial epicondylitis, release of the posterior and other compartments of the leg, forearm fascia release for fascial compartment syndrome, release of fascial compartments in the upper or lower extremities, relieving the compression of a nerve by a ligament pulley or tunnel, and releasing the travel of a ligament or tendon through a pulley or tunnel. Additional endoscopic procedures that can be performed with a cannula or device of the present application include endoscopic surgical procedures on the spine, such as endoscopic discectomy for the treatment of degenerative disc disease, herniated discs, bulging discs, pinched nerves or sciatica. Endoscopic procedures that can be performed with a cannula or device of the present application also include endoscopic procedures on cranial and facial tissues, as well as fasciotomy or fascia release throughout the body. The cannula or device of the present application can be used for blood vessel, including vein or artery, harvesting throughout the body, for example to provide blood vessel graft material in conjunction with a coronary bypass procedure or for a reconstructive surgical procedure. Endoscopic procedures that can be performed with a cannula or device of the present application also include endoscopic procedures on the foot, wrist and hand, including the palmar and dorsal sides of the hand. Endoscopic procedures that can be performed with a cannula or device of the present application on the hand also include the digits, including the thumb, index finger, middle finger, ring finger and little (pinky) finger.

Endoscopic surgical procedures that can be performed with a device of the present application, such as, but not limited to, a tunnel release procedure or pulley release, can be performed by approaching the target tissue through an incision or body opening on either the proximate or distal side of the target tissue.

One aspect of the present application relates to an endoscopic surgical blade assembly. The endoscopic surgical blade assembly comprises an endoscopic surgical blade having a distal end, a proximal end, a top edge, a bottom edge and one or more cutting surfaces at the distal end, the blade being structurally configured for attachment to the distal end of an endoscope; and a protective shield attached to the blade above the one or more cutting surfaces and extending away from the distal end of the blade.

In some embodiments, the shield comprises a single piece of solid planar material.

In some embodiments, the shield is attached to the top edge of the blade. In some embodiments, the shield is welded to the blade. In some embodiments, the shield is attached to the top edge of the blade so that the planar cross-section of the frame is substantially perpendicular to the top edge of the blade. In some embodiments, the shield defines a plane that is perpendicular to the one or more cutting surfaces of the blade. In some embodiments, the thickness of the shield component is between about 0.2 mm and about 1 mm. In some embodiments, the shield extends at least 4 mm beyond the distal end of the blade.

In some embodiments, the cutting surface of the blade comprises an upper cutting surface and a lower cutting surface, wherein the upper cutting surface and the lower cutting surface meet at a crotch therebetween. In some embodiments, the lower edge of the blade comprises a horizontal mounting surface for affixing the blade onto a knife tube to form an endoscopic knife assembly. In some embodiments, the endoscopic knife assembly further comprises a knife tube having a distal end and a proximal end, wherein the blade is mounted on the distal end of the knife tube. In some embodiments, the endoscopic knife assembly further comprises a handle at the proximal end of the knife tube. In some embodiments, the knife tube comprises an alignment ring attached near the proximal end and one or more slots at the proximal end for the attachment of a locking assembly to the knife tube and alignment ring.

Another aspect of the present application relates to an assembly comprising an endoscopic surgical blade and a shield component, wherein said shield component attaches to the top edge of a surgical blade in a plane that is perpendicular to the cutting surface of the blade and wherein the longer axis of the shield component extends horizontally in the proximal and distal directions and the shorter axis of the shield component extends horizontally in each lateral direction, and wherein the blade is sized to fit at a tip of an endoscope.

In some embodiments, the blade is a low-profile blade.

In some embodiments, the blade comprises an upper cutting surface and a lower cutting surface at its distal end and having a non-cutting radiused surface at the top end of the upper cutting surface, wherein said upper cutting surface and said lower cutting surface meet at a crotch therebetween, further wherein the blade is sized to fit at a tip of an endoscopic viewing device.

In other embodiments, the blade has a single cutting surface, wherein the cutting surface is slanted such that the top of the cutting surface leads the bottom of the cutting surface.

In still other embodiments, the blade has a single cutting surface, wherein the cutting surface is slanted such that the bottom of the cutting surface leads the top of the cutting surface. In yet another embodiment, the low-profile blade has a single cutting surface and is semi-circular or concave in shape.

In some embodiments, the blade has a sloped top surface, being tallest near the cutting surface and sloping downwards towards the knife tube along its length.

In one embodiment, the low-profile blade further comprises a horizontal mounting surface for affixing the blade onto a knife tube to form an endoscopic knife assembly.

Another aspect of the present application relates to an endoscopic knife assembly, comprising: a knife tube having a distal end and a proximate end, a blade mounted at the distal end of the knife tube and a shield component, wherein said shield component attaches to the top edge of a surgical blade in a plane that is perpendicular to the cutting surface of the blade and wherein the longer axis of the shield component extends horizontally in the proximal and distal directions and the shorter axis of the shield component extends horizontally in each lateral direction, and wherein the blade is sized to fit at a tip of an endoscope.

In one embodiment, the endoscopic knife assembly further comprises a handle at the proximal end of the knife tube.

In another embodiment, the knife tube comprises an alignment ring attached near the proximate end and one or more slots at the proximate end for the attachment of a locking assembly to the knife tube and alignment ring.

In another embodiment, the knife tube is marked on at least one surface with gradations.

In another embodiment, the shield component is welded to the blade.

In another embodiment, the blade is welded to the knife tube.

Another aspect of the present application relates to an instrument kit for implementing an endoscopic surgical procedure comprising: an endoscopic knife assembly, comprising: a knife tube having a distal end and a proximate end, a blade mounted at the distal end of the knife tube and a shield component, wherein said shield component attaches to the top edge of a surgical blade in a plane that is perpendicular to the cutting surface of the blade and wherein the longer axis of the shield component extends horizontally in the proximal and distal directions and the shorter axis of the shield component extends horizontally in each lateral direction, and wherein the blade is sized to fit at a tip of an endoscope.

In some embodiments, the kit further comprises a cover for the endoscopic knife assembly.

In other embodiments, the endoscopic knife assembly further comprises a handle at the proximal end of the knife tube.

In still other embodiments, the knife tube comprises an alignment ring attached near the proximate end and one or more slots at the proximate end for the attachment of a locking assembly to the knife tube and alignment ring.

In yet other embodiments, the instrument kit further comprises a cannula having an open slot extending along the length of the cannula. In a related embodiment, the cannula is a clear cannula. In another related embodiment, the cannula has an inner diameter of between about 2.4 mm and about 3.0 mm. In a further embodiment, the cannula has an inner diameter of about 2.7 mm. In a separate related embodiment, the cannula has an inner diameter of between about 3.7 mm and about 4.3 mm. In a further embodiment, the cannula has an inner diameter of about 4.0 mm.

In other embodiments, the instrument kit further comprises an obturator, an elevator and/or an arthroscope.

Another aspect of the present application relates to a method for uniportal endoscopic division of a target tissue, comprising: establishing an entry portal at a location proximate to and proximal or distal of the target tissue; inserting a cannula having open proximal and distal ends and an open slot extending along the length of the cannula, wherein the open slot faces the target tissue; inserting an endoscopic viewing device into the cannula, said endoscopic viewing device comprising an endoscopic knife assembly, comprising: a knife tube having a distal end and a proximate end, a blade mounted at the distal end of the knife tube and a shield component, wherein said shield component attaches to the top edge of a surgical blade in a plane that is perpendicular to the cutting surface of the blade and wherein the longer axis of the shield component extends horizontally in the proximal and distal directions and the shorter axis of the shield component extends horizontally in each lateral direction, and wherein the blade is sized to fit at a tip of an endoscope; advancing said endoscopic viewing device through the cannula so that the blade and shield component protrude through the slot and move into the proximity of the target tissue, the shield component intervening between the target tissue and an overlying tissue; operatively engaging the target tissue with the cutting surface of the blade; advancing the blade through the cannula to divide the target tissue, such that the shield component prevents the cutting of the overlying tissue.

In some embodiments, the method for endoscopic division of a target tissue is a method for treating trigger finger, wherein the target tissue is the A1 pulley.

In other embodiments, the method for endoscopic division of a target tissue is a method for treating carpal tunnel syndrome, wherein the target tissue is the transverse carpal ligament.

In still other embodiments, the target tissue is fascia.

In some embodiments, the cannula is made of a transparent material.

In still other embodiments embodiment, the step of inserting an endoscopic viewing device comprising an endoscopic knife assembly having a low-profile blade and a shield component is preceded by the insertion of another endoscopic viewing device to visualize anatomic structures surrounding the cannula.

In some embodiments, the blade has a sloped top surface, being tallest near the cutting surface and sloping downwards towards the knife tube along its length. The sloped top surface allows the blade described herein to maintain a low profile such that it can be used with a slotted cannula for the precise division of a target tissue and to be easily withdrawn again from the tissue without damaging other tissues.

In one embodiment, the low-profile blade further comprises a horizontal mounting surface for affixing the blade onto a knife tube to form said endoscopic knife assembly.

In another embodiment, the top surface of the blade is angled downward towards the proximate end of the blade.

In another embodiment, the blade body comprises a notch on the lower edge to engage with a knife tube.

Another aspect of the present application relates to an endoscopic knife assembly, comprising: a knife tube having a distal end and a proximate end and a low-profile blade at its distal end wherein a shield component is attached to the upper edge of the blade.

In one embodiment, the endoscopic knife assembly further comprises a handle at the proximal end of the knife tube.

In another embodiment, the knife tube comprises an alignment ring attached near the proximate end and one or more slots at the proximate end for the attachment of a locking assembly to the knife tube and alignment ring.

Another aspect of the present application relates to a low profile cover for an endoscopic knife assembly comprising a shield component.

In one embodiment, the cover is shaped to fit over the shield component, protecting the shield component and the blade from contact when not in use. In some embodiments, the side of the cover extend downward and grip the sides of the tube of the knife blade assemble, thereby securing the cover in place. In some embodiments, the cover has a handle on top for gripping and removing the cover from the endoscopic knife assembly comprising a shield component.

The presently described low-profile blade and shield component is sized to fit at the tip of an endoscopic viewing device and form a component of an endoscopic knife assembly, wherein the blade is welded onto a hollow knife tube that allows the practitioner to extend an endoscopic camera through the hollow knife tube to allow direct visualization of the tissue and blade before, during and after the cutting of the target tissue.

Particular embodiments of the endoscopic knife assembly further comprise a handle at its proximal end that allows the direct manual manipulation of the endoscopic knife assembly. The handle also comprises a hollow lumen that allows an arthroscope to be passed through the handle into the knife tube, allowing direct visualization of the tissue and blade before, during and after the cutting of the target tissue. Other embodiments of the knife tube assembly comprise an alignment ring and slots at the proximate end to allow the knife tube assembly to be mated with the locking mechanism of an endoscopic surgical system.

The design of the present blade and shield component is such that it is usable in endoscopic surgery in a manner that allows the practitioner to extend the blade through the cannula to the target tissue without damage to surrounding tissue and/or organs. The blade and shield component are made from materials commonly used for surgical blades or scalpels, such materials include, but are not limited to, hardened and tempered steel, stainless steel, high carbon steel, titanium, alloys and ceramic.

In particular embodiments, the blade and shield component are made from stainless steel. In a further embodiment, the stainless steel is martensitic stainless steel. An exemplary martensitic stainless steel is Bohler-Uddeholm AEB-L martensitic stainless steel. In a still further embodiment, the martensitic stainless steel is heat-treated. In another further embodiment, the stainless steel is 440 A stainless steel. In a particular embodiment, the and shield component are made from Hitachi GIN-5 SST-MODIFIED 440-A stainless steel. The and shield component are optionally flash electropolished. Cutting edges are machine finished and must be sharp. In a particular embodiment, the steel of the blade and shield component are heat-treated to Rockwell C hardness of about 50-72. In a more particular embodiment, the steel of the blade and shield component are heat-treated to Rockwell C hardness of 58-64.

FIG. 1A depicts a top view of an embodiment of the shield component 100 of the endoscopic knife assembly, showing an exemplary, but non-limiting, shape of the shield component 100.

In some embodiments, the length 101 of the shield component 100 from its distal end 102 to its proximal end 103 is between about 4 mm and about 15 mm. In some further embodiments, the length 101 of the shield component 100 from its distal end 102 to its proximal end 103 is between about 5 mm and about 10 mm. In some still further embodiments, the length 101 of the shield component 100 from its distal end 102 to its proximal end 103 is between about 6 mm and about 9 mm. In yet further embodiments, the length 101 of the shield component 100 from its distal end 102 to its proximal end 103 is about 7.5 mm.

Still referring to FIG. 1A, the lateral width 104 of the shield component 100 from its distal end 102 to its proximal end 103 is between about 2 mm and about 8 mm. In some further embodiments, the width 104 of the shield component 100 is between about 2 mm and about 6 mm. In still further embodiments, the width 104 of the shield component 100 is between about 2 mm and about 4 mm. In yet further embodiments, the width 104 of the shield component 100 is about 3 mm.

In some embodiments, the distal end 103 of the shield component 100 is radiused 105 from its sides 106 to the distal end 103. In some embodiments, the distal end 103 is pointed where the radii 105 meet. In other embodiments, the distal end 103 is rounded where the radii 105 meet. In still other embodiments, the radii 105 do not meet and the distal end 103 has a flat surface perpendicular to the sides 106.

Also in FIG. 1A, some embodiments of the shield component 100 comprise a slot 107 for attaching the shield component to a blade. In general, the inside width of the slot 107 matches the outside width of the blade so that there is no space between them when assembled and the shield component 100 can be securely attached to the blade. In some embodiments, the width of the slot 107 is between about 0.2 mm and about 1 mm. In some further embodiments, the width of the slot 107 is between about 0.4 mm and about 0.8 mm. In some still further embodiments, the width of the slot 107 is between about 0.5 mm and about 0.75 mm. In some yet further embodiments, the width of the slot 107 is about 0.64 mm.

In some embodiments, the sides 106 of the shield component 100 are partially tapered 108, narrowing towards the proximal end 102 to meet the slot 107 at the proximal end 102.

Turning now to FIG. 1B, a side view of an exemplary shield component is shown. In some embodiments the thickness 109 of the shield component 100 is between about 0.2 mm and about 1 mm. In some further embodiments, the thickness 109 is between about 0.4 mm and about 0.8 mm. In some still further embodiments, the thickness 109 is between about 0.5 mm and about 0.75 mm. In some yet further embodiments, the thickness 109 is about 0.64 mm.

FIGS. 2A-B show an endoscopic assembly knife tube assembly 400 with a shield assembly 100 attached to the top surface of a blade 200 that, in turn, is mounted on a knife tube 300. The blade 200 is attached to and exemplary knife tube 300 having an alignment ring 350, such that the blade 200 is welded to the knife tube 300.

The knife tube 300 can optionally be marked on the top or side surface with gradations as exemplified in FIG. 2A to show the distance to the distal end of the knife tube 300, or to a specific point on the leading edge of the cutting surface of the blade 200. As a non-limiting example, major gradations 301 can be made to show each centimeter in distance from the cutting surface of the blade 200, with minor gradations 302 between them to, for example, show each 1, 2, 2.5 or 5 millimeters. While the gradations can be applied to the knife tube 300 by any means known in the art, it is preferable to lasermark the gradations on the knife tube 300 for accuracy and permanence. Additionally, the knife tube 300 can also be marked in a similar manner with additional information, for example on the bottom or a side surface of the knife tube 300. Exemplary markings may include, but are not limited to, a maker's mark, part number, lot number and an indication that the endoscopic knife assembly is intended for only a single use.

Referring to FIGS. 2A-B, showing top and side views of the endoscopic knife assembly, an alignment ring 350 is affixed near the proximate end of the knife tube 300. In one embodiment, the alignment ring 350 is affixed in position on the knife tube 300 using USP Class VI gamma irradiation and steam resistant epoxy adhesive during assembly. In some embodiments, a two part epoxy such as MASTER-BOND EP42 HT™ or ARMSTRONG C-7™, or a suitable equivalent thereof is used. In one embodiment, the distance 303 between the alignment ring 350 and the proximate end of the knife tube 300 is between about 15 mm and about 25 mm. In another embodiment, the distance 303 is between about 18.9 mm and about 19.66 mm. In another embodiment, the distance 303 is about 19.28+/−0.38 mm.

As shown in FIGS. 2A-B, in particular embodiments, the alignment ring 350 comprises a flattened surface 351 that is aligned on the same side of the knife tube 300 as the blade 200. The plane of the flattened surface 351 of the alignment ring 350 is oriented perpendicular to the plane in which the blade 200 is affixed to the knife tube 300.

The knife tube 300 further comprises slots 304 in the proximate end that are positioned on the sides of the knife tube 300, perpendicular to the blade 200 mounted on the top of the knife tube 300. The slots 304 in particular embodiments extend forward to where the alignment ring 350 is affixed to the knife tube 300. In some applications, the slots 304 may not extend forward to where the alignment ring 350 is affixed to the knife tube 300. In one embodiment, the slots 304 have a width of between about 0.4 mm and about 1.1 mm wide, more particularly between about 0.53 mm and about 0.91 mm wide. In some embodiments, the width of the slots 304 is about 0.66 mm.

The slots 304 and alignment ring 350 provide an attachment point for a locking device, in order to mount an endoscope to the scope-mounting blade or endoscopic knife assembly.

Also referring to FIG. 2A-B, in some embodiments, the width or outer diameter of the knife tube is such that it will fit and slide easily within a cannula having an inner diameter of about 4 mm, yet will be held securely by said cannula, such that the knife tube does not experience significant side-to-side and/or up-and-down play.

Referring to FIGS. 2A-B, in some embodiments, the knife tube 300 has a flared proximate end 305. In one embodiment, about 0.2 to about 0.5 most proximate millimeters of the knife tube 300 are flared. In another embodiment, about the 0.38 most proximate millimeters of the knife tube 300 are flared. In another embodiment, the flared proximate end 305 has a flare angle of about 20 to 40 degrees, more particularly about 30 degrees.

Figure 3:
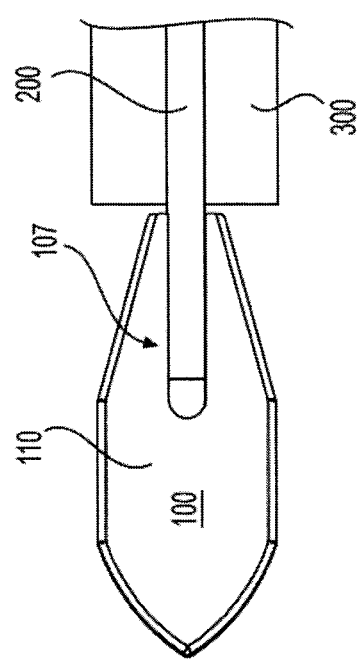
FIG. 3 is a magnified view of an embodiment of a shield component attached to an endoscopic knife assembly.
Figure 5C:
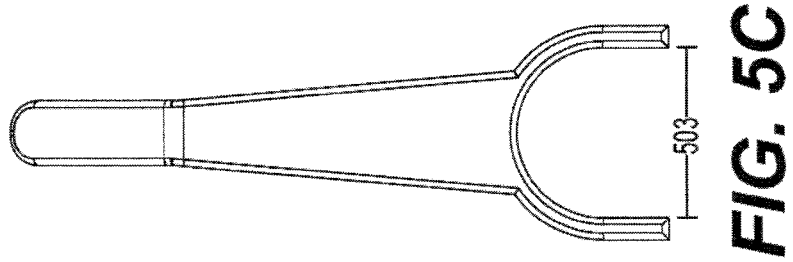
Figure 5B:
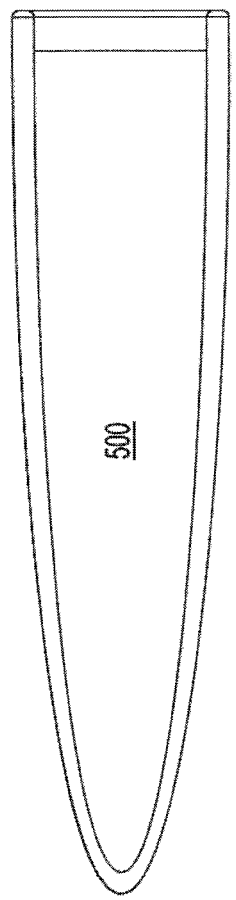

Referring now to FIG. 3, a detail is shown of the arear encircled by "X" in FIG. 2A. The shield component 100 is shown attached to the blade 200 at the slot 107 in the shield component. The top surface 110 of the shield component 100 is flush with the top surface 201 of the blade 200. The blade 200, in turn, is mounted on the knife tube 300.

FIG. 4 is an illustration depicting the endoscopic knife assembly viewed at an angle and showing the mounting of the shield component 100 to the blade 200 and the blade 200 welded onto the knife tube 300.

FIGS. 4A-C depict side, bottom and proximal end views, respectively, of an exemplary low profile protective cover 500 for an endoscopic knife assembly comprising a shield component as described herein. In general, the shape of the cover is determined by the shape of the shield assembly and the overall configuration of the knife tube assembly.

As shown in FIG. 4A, the sides 501 of the low profile cover extend down in order to protect the blade from contact with object while the blade is in storage or transport. The low profile cover 500 also has a handle 502 for lifting the low profile cover 500 off of the knife tube assembly.

FIG. 4B shows a bottom view of the low profile cover 500, generally showing that the shape of the cover is determined by the shape of the shield assembly and the overall configuration of the knife tube assembly.

FIG. 4C depicts a proximal end view of a low profile cover 500 as described herein. In some embodiments, the handle 502 is attached at the proximal end of the low profile cover 500. In addition, the width of the opening 503 within the cover 500 is such that it grips the sides of the knife tube securely enough that the cover 500 does not fall off the knife tube assembly due to shaking or casual contact, for example, but is easily removable when the handle 502 is lifted.

Kit

Another aspect of the present application relates to an instrument kit for implementing an endoscopic surgical procedure. The instrument kit contains an endoscopic knife assembly having a low-profile blade with a shield component attached thereto. In some embodiments, the instrument kit comprises components and implements useful for endoscopic procedures. In one embodiment, the instrument kit contains a cannula. In a related embodiment, the cannula is transparent. In another related embodiment, the cannula includes a longitudinal bore having open proximal and distal ends and an open slot extending along the length thereof communicating with the open ends. In another related embodiment, the instrument kit include an elongate insertion member, such as an obturator, that is slidably receivable within the cannula guide member and is configured so that at least portions thereof conform with the open distal end and the open slot of the guide member to form a smooth exterior surface in combination therewith.

In one embodiment, the instrument kit further includes an endoscope or endoscopic viewing device sized for insertion into the cannula guide member for direct visualization of an operative site.

In one embodiment, the instrument kit further includes an endoscope sized for insertion into the cannula guide member for direct visualization of an operative site.

In another embodiment, the endoscope is capable to carry a cutting instrument at a leading end. The endoscope is insertable into the cannula guide member such that the cutting instrument protrudes through the open slot in the cannula guide member.

In another embodiment, the instrument kit further includes an elevator.

In another embodiment, the instrument kit further includes a depth gauge mountable to a leading end of the endoscope.

In another embodiment, the instrument kit further includes a locking device capable of locking the endoscope and the cannula guide member into mutually fixed positions.

In another embodiment, the instrument kit further includes a stop device mountable on the cannula guide member to prevent excessive penetration at a surgical site by the cutting instrument.

In another embodiment, the instrument kit further includes a curved dissector.

Methods

Another aspect of the present application relates to a method for uniportal endoscopic surgery. Uniportal endoscopic surgery allows the practitioner to visualize a target tissue and its surrounding tissues as well as perform a surgical procedure through a single entry portal. In some instances, the entry portal may be a natural opening, while in other instances the entry portal is an incision. In the case of an incision, generally only a single small incision must be made. In particular embodiments, the incision is less than or equal to about 2 cm in length. In more particular embodiments, the incision is less than or equal to about 1.5 cm in length. In still more particular embodiments, the incision is less than or equal to about 1 cm in length. The single small incision allows the patient to recover more quickly and begin therapy and/or resume normal activity as tolerated sooner.

The uniportal endoscopic surgical procedure described herein can be used to implement a number of different surgical procedures. In some embodiments, the uniportal endoscopic surgical procedure is selected from the group consisting of trigger finger release, carpal tunnel release, cubital tunnel release, plantar fascia release, lateral release for patella realignment, release of the extensor tendons, release of the posterior and other compartments of the leg, and forearm fascial release.

One embodiment of the present application relates to a method for a performing a uniportal endoscopic surgical procedure a target tissue in a subject. Generally, following the establishment of an entry portal, in some embodiments a blunt instrument, such as an elevator is inserted through the portal to establish an opening in the underlying tissue between the portal and the target tissue.

A cannula having open proximal and distal ends and an open slot extending along the length of the cannula is inserted into the entry portal and extended through to the target tissue. In some embodiments, the cannula is made of a clear plastic material so that the entirety of the surrounding tissue can be viewed with an arthroscope. In some embodiments, in order to facilitate insertion of the cannula, the central lumen of the cannula comprises an obturator, which is withdrawn following insertion of the cannula. In other embodiments, the design of the cannula is such that a separate obturator is not needed.

In some embodiments, the cannula has an inner diameter of between about 2.0 mm to about 3.5 mm. In further embodiments, the cannula has an inner diameter of between about 2.4 mm to about 3.0 mm. In a particular embodiment, the cannula has an inner diameter of about 2.7 mm.

In some other embodiments, the cannula has an inner diameter of between about 3.3 mm to about 4.7 mm. In further embodiments, the cannula has an inner diameter of between about 3.7 mm to about 4.3 mm, in a particular embodiment, the cannula has an inner diameter of about 4.0 mm.

An endoscopic viewing device is inserted into the cannula to view the target tissue and the surrounding tissues, assuring that the slot of the cannula is in proper orientation to the target tissue. The endoscopic viewing device is withdrawn and an endoscopic viewing device with a mounted endoscopic knife assembly having a low-profile blade and a shield component attached thereto is advanced into the cannula, with the knife blade aligned with the slot of the cannula. In some embodiments, the endoscopic viewing device used for viewing the target tissue and the surrounding tissues is the same unit as the endoscopic viewing device comprising a mounted endoscopic knife assembly. In other embodiments, the endoscopic viewing device used for viewing the target tissue and the surrounding tissues is a different unit from the endoscopic viewing device comprising a mounted endoscopic knife assembly.

The endoscopic viewing device comprising a mounted endoscopic knife assembly is advanced further through the cannula so that the blade moves in contact with the target tissue through the slot, operatively engaging the target tissue with the blade and the shied assembly is in contact with the side of the target tissue opposite the cannula. Accordingly, the shield component will lie between the target tissue and the adjacent overlying tissue. The blade is further advanced through the cannula to divide the target tissue. The shield component slides along with the blade, remaining between the target tissue and the overlying tissue, preventing damage to the overlying tissue.

In one particular embodiment, the operative procedure is trigger finger release.

In another particular embodiment, the establishing an entry portal comprises making an incision.

In another particular embodiment, the target tissue is the A1 pulley.

In another particular embodiment, the inserting of said endoscopic viewing device comprising an endoscopic knife assembly having a low-profile blade and a shield component attached thereto is followed by the insertion of an endoscopic viewing device comprising a means for visualization of the results of the endoscopic surgical procedure on the target tissue.

The present invention is further illustrated by the following examples which should not be construed as limiting. The contents of all references, patents and published patent applications cited throughout this application, as well as the Figures and Tables, are incorporated herein by reference.

Example 1: Uniportal Endoscopic Trigger Release

In a patient presenting with trigger finger of the middle or ring finger, a 1 cm incision is made just proximal to the A1 pulley on the distal palmar crease proximate to the affected digit.

An elevator is introduced into the incision and used to create a plane superficial to the flexor tendon sheath. The elevator is withdrawn.

A slotted cannula with an obturator inserted therein is introduced into the incision and advanced through the plane created by the elevator. The slot of the cannula is oriented facing the flexor tendon sheath. The obturator is removed from the cannula.

An endoscopic viewing device is introduced into the cannula and advanced to visualize the A1 pulley and A2 pulley. The endoscopic viewing device is withdrawn.

An endoscopic knife assembly having a low-profile blade having a shield component attached thereto is fastened onto an endoscopic viewing device.

The scope and blade assembly is advanced into the cannula, dividing the A1 pulley. Having the endoscopic knife assembly mounted directly on the endoscopic viewing device allows direct visualization of the procedure from the point-of-view of the blade, allowing visualization of the A2 pulley and avoiding damage to the A2 pulley. The scope and blade assembly is withdrawn from the cannula.

An endoscopic viewing device is again advanced into the cannula to visualize the cut edges of the A1 pulley, as well as visualization of the underlying flexor tendon.

While visualizing the tendon, release of the tendon is confirmed by passive manipulation of the digit through its range of motion.

The absence of triggering is confirmed by having the subject flex and extend the affected digit.

The endoscopic viewing device is withdrawn and the cannula is removed from the incision.

The wound is closed and a soft bandage is applied.

The patient is encouraged to begin early finger motion following surgery and to resume daily activities as tolerated.

The above description is for the purpose of teaching the person of ordinary skill in the art how to practice the present invention, and it is not intended to detail all those obvious modifications and variations of it which will become apparent to the skilled worker upon reading the description. It is intended, however, that all such obvious modifications and variations be included within the scope of the present invention, which is defined by the following claims. The claims are intended to cover the components and steps in any sequence which is effective to meet the objectives there intended, unless the context specifically indicates the contrary.

What is claimed is:

1. An endoscopic surgical blade assembly comprising:
    an endoscope, and
    an endoscopic surgical blade mounted between a bottom mounting portion and a top shield portion, wherein the endoscopic surgical blade comprises a distal end, a proximal end, and one or more cutting surfaces at the distal end,
    wherein the one or more cutting surfaces includes a straight cutting edge,
    wherein the shield portion is fixedly attached to the blade above the one or more cutting surfaces and extends away from the distal end of the blade, and
    wherein the endoscope allows visualization of the blade upon advancement of the endoscope along the bottom mounting portion until a distal end of the endoscope reaches the endoscopic surgical blade so that the blade fits at a tip of the endoscope.

2. The endoscopic surgical blade assembly of claim 1, wherein the top shield portion comprises a single piece of solid planar material.

3. The endoscopic surgical blade assembly of claim 1, wherein the top shield portion is attached to a top edge of the blade.

4. The endoscopic surgical blade assembly of claim 3, wherein the top shield portion is attached to the top edge of the blade so that the planar cross-section of the shield is substantially perpendicular to the top edge of the blade.

5. The endoscopic surgical blade assembly of claim 1, wherein the top shield portion is welded to the blade.

6. The endoscopic surgical blade assembly of claim 1, wherein the thickness of the top shield portion is between about 0.2 mm and about 1 mm.

7. The endoscopic surgical blade assembly of claim 1, wherein the top shield portion defines a plane that is perpendicular to the one or more cutting surfaces of the blade.

8. The endoscopic surgical blade assembly of claim 1, wherein the top shield portion extends at least 4 mm beyond the distal end of the blade.

9. The endoscopic surgical blade assembly of claim 1, wherein the one or more cutting surfaces of the blade comprises an upper cutting surface and a lower cutting surface, wherein the upper cutting surface and the lower cutting surface meet at a crotch therebetween.

10. The endoscopic surgical blade assembly of claim 1, wherein the bottom mounting portion is a knife tube, and wherein a bottom edge of the blade comprises a horizontal mounting surface for affixing the blade onto the knife tube.

11. The endoscopic surgical blade assembly of claim 1, wherein the bottom mounting portion is a knife tube, and the knife tube has a distal end and a proximal end, wherein the blade is mounted on the distal end of the knife tube.

12. The endoscopic surgical blade assembly of claim 11, further comprising a handle at the proximal end of the knife tube.

13. The endoscopic surgical blade assembly of claim 11, wherein the knife tube comprises an alignment ring attached near the proximal end and one or more slots at the proximal end for the attachment of a locking assembly to the knife tube and alignment ring.

14. An instrument kit for implementing an endoscopic surgical procedure comprising:
    the endoscopic surgical blade assembly of claim 1; and
    a cannula having an open slot extending along the length of the cannula.

* * * * *